Figure 1:
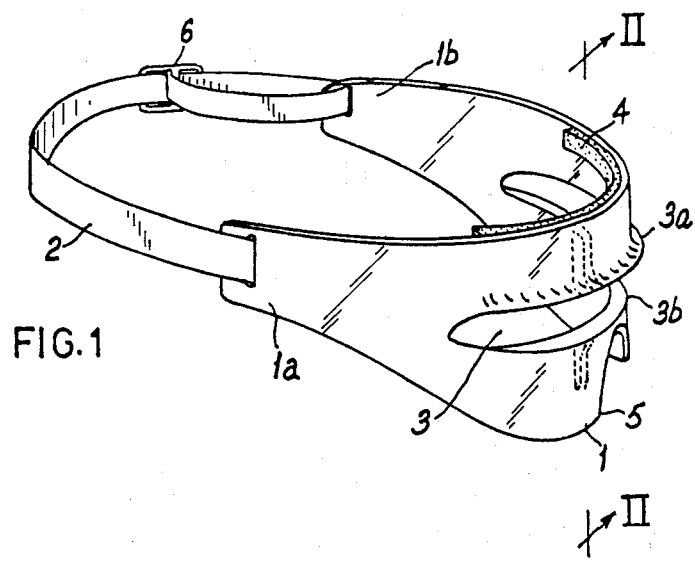

United States Patent [19]

Ainsworth et al.

[11] Patent Number: 4,494,251
[45] Date of Patent: Jan. 22, 1985

[54] EYE PROTECTOR

[76] Inventors: Leslie Ainsworth, Flat 2, 2, King's Gardens, Hove, Sussex BN3 2PE; Harold Ainsworth, Radbrook Hall Hotel, Radbrook Rd., Shrewsbury, Shropshire, SY3 9BR, both of England

[21] Appl. No.: 374,595
[22] Filed: Apr. 30, 1982

[30] Foreign Application Priority Data

Apr. 30, 1981 [GB] United Kingdom ............... 8113353
Oct. 8, 1981 [GB] United Kingdom ............... 8130444

[51] Int. Cl.³ ............................................. A61F 9/02
[52] U.S. Cl. ........................................ 2/425; 2/426; 2/443; D2/234
[58] Field of Search ............ 2/9, 425, 431, 433, 2/439, 426, 443, 427, 424, 2.5; D2/234

[56] References Cited

U.S. PATENT DOCUMENTS

| 177,229 | 3/1956 | Grace | D2/234 |
|---|---|---|---|
| 1,336,009 | 4/1920 | Wilmer | 2/431 |
| 1,523,521 | 1/1925 | Goodman | 2/9 |
| 1,954,184 | 4/1934 | Schlumbohm | 2/433 |
| 2,418,376 | 4/1947 | Turner | 2/9 |
| 2,914,769 | 1/1959 | Anderson | 2/9 |
| 3,527,461 | 9/1970 | Prater | 2/424 |
| 3,707,004 | 12/1972 | Kapitan et al. | 2/2.5 |
| 4,288,878 | 9/1981 | Helmbreck | 2/431 |
| 4,367,561 | 1/1983 | Solari | 2/9 |

FOREIGN PATENT DOCUMENTS

| 14243 | 7/1908 | United Kingdom | 2/433 |
|---|---|---|---|
| 329470 | 5/1930 | United Kingdom | 2/433 |
| 847365 | 9/1960 | United Kingdom | 2/433 |

OTHER PUBLICATIONS

International Patent Publication, 47908; Aug. 1979, Wichers, Max F., pp. 2-427.

Primary Examiner—Henry S. Jaudon
Assistant Examiner—Steven N. Meyers
Attorney, Agent, or Firm—Michael J. Striker

[57] ABSTRACT

An eye protector (e.g. for squash players) comprises a screen slitted in the eye region of the wearer and with at least one thickened region adjacent to the slit(s) to reinforce the screen and prevent a resilient object (e.g. a squash ball) intruding through the slit and contacting a wearer's eye. Thickened regions can be provided above and below the slit(s) on the outward facing surface of the screen and the upper region can be thicker than the lower. An elasticated band can hold the screen over the wearer's eye region.

4 Claims, 7 Drawing Figures

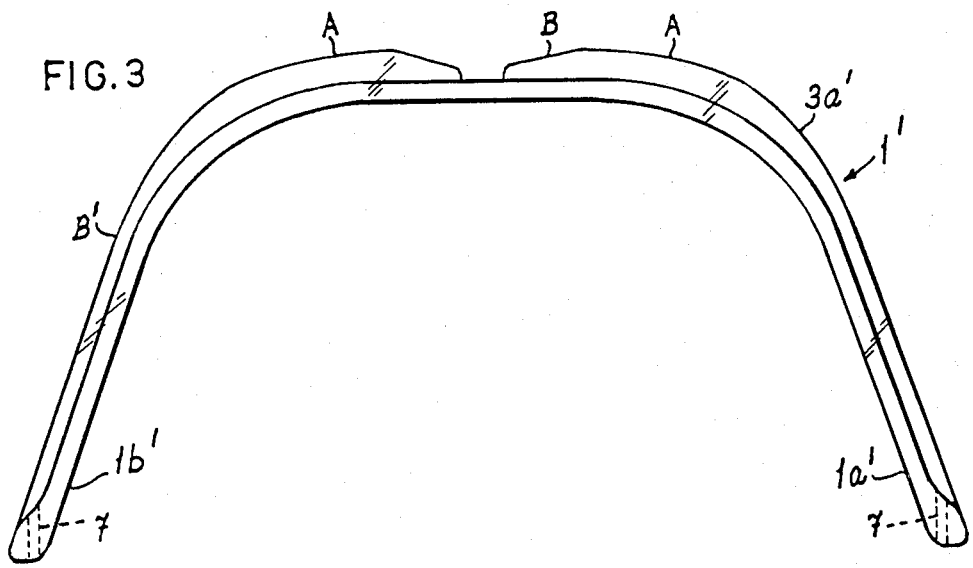
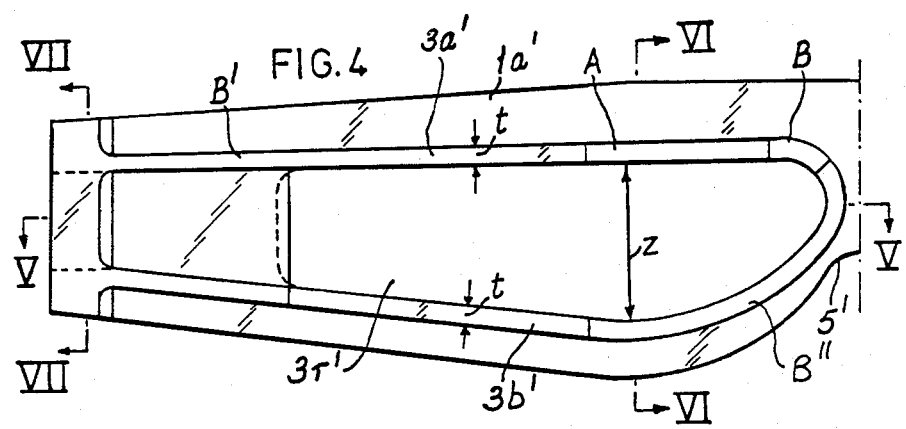
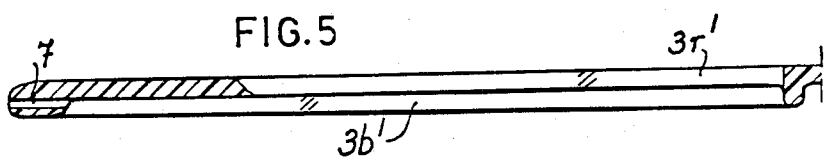
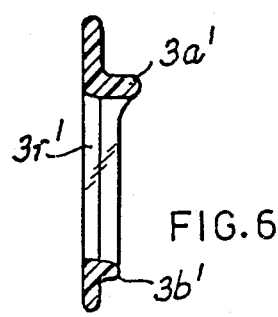
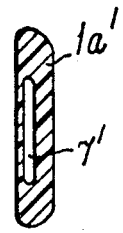

EYE PROTECTOR

This invention relates to an improved eye protector which has particular, but not exclusive, application to preventing eye damage to sports players, and especially to squash players.

The size of a squash ball and the speed with which it moves in a squash court during playing a game of squash give rise to a high risk of eye damage to squash players. Protective goggles which completely screen the eyes will eliminate the risk of eye damage by contact with the ball, but impede visibility to an unacceptable extent, particularly when the goggles become misted during the exertion of play, and are generally uncomfortable to wear.

To avoid the need for a player to have to view the court through a transparent sheet which might distort the view and/or partially obscure it, it has been proposed to use an eye protector in the form of a screen having a slit centered on the pupils which is narrower than the diameter of a squash ball. Such a slitted protector has the advantages of ensuring there is no distortion of the player's direct forward view and the eye regions can be properly ventilated to avoid discomfort during strenuous play.

To ensure that a slitted protector provides the maximum protection, the width of the slit should be as narrow as possible and the spacing of the slit from the eyeballs should be as great as possible. Further the slitted screen material must be rigid enough to resist deformation under impact from a fast moving squash ball.

On the contrary, to provide the minimum interference to the vision of the player, the slit should be as wide as possible and the spacing of the slit from the eyeballs should be as small as possible.

To provide adequate rigidity a thick screen must be used, which adds to the weight of the protector.

The present invention seeks to provide a slitted eye protector which resolves these contradictory requirements for safety and vision in an original way.

According to the invention a slitted eye protector includes at least one thickened region adjacent to the slit and suitably defining the upper extremity of the slit.

Thickened regions may be provided both above and below the slit and these need not be of the same thickness. In the case where the thickened regions project outwardly, and one thickened region is significantly thicker than the other, the probability of a squash ball intruding into the slit is reduced, since it will be deflected away from the thicker region before it contacts the thinner region. Desirably, the upper region is made thicker than the lower.

The provision of at least one thickened region, strengthens the protective screen in the critical ball-contact area without unduly adding to the weight of the protector and if it projects away from the eye it increases the effective spacing of the ball-contact area from the eyeballs.

The screen can be made from any convenient tough material, suitably a plastics material such as polycarbonate, ABS, PVC, acrylic or polyethylene. Desirably the screen is transparent and can be coloured.

Any convenient means can be provided for supporting the screen over the eye region and one suitable means comprises side pieces which pass round the sides of the forehead and are linked together by a resilient strap (suitably of adjustable length) passing around the back of the head.

The slit of the protector may be divided into two separate slits, one for each eye, the connecting bridge between the slits then serving to protect the nose of the wearer. In the case of a protector for a squash player, this connecting bridge serves to prevent intrusion of an edge of a squash racquet.

The lower edge of the screen can be contoured to accommodate the nose and may be shaped to rest smoothly on the cheeks. Optionally a resilient pad can support the screen on the forehead.

Figure 2:
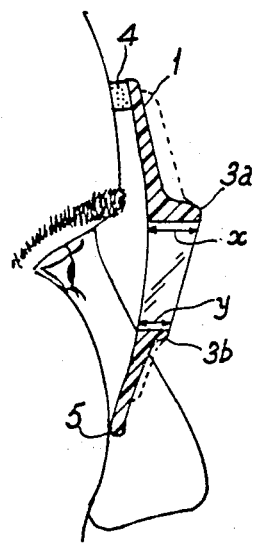

The invention will now be further described, by way of example, with reference to the accompanying drawings, in which:

FIG. 1 is a perspective view of a first embodiment of eye protector in accordance with the invention designed for a squash player, FIG. 2 is a section on the line II—II of FIG. 1, with the protector in place on a player, FIG. 3 is a plan of the rigid portion of a second embodiment of protector in accordance with the invention also designed for a squash player, FIG. 4 is a developed view of the left-hand half of the protector shown in FIG. 3, and FIGS. 5, 6 and 7 are sections on the lines V—V, VI—VI and VII—VII, respectively of FIG. 4.

The protector shown in FIGS. 1 and 2 consists of a screen 1 curved at the sides and a resilient strap 2. The screen is provided with a slit 3 flanked above and below by thickened regions in the form of ribs 3a and 3b, respectively, the upper rib 3a having a greater height (i.e. a greater projection from the front surface of the screen 1) than the lower rib 3b.

A resilient pad 4 is provided on the forehead region of the screen 1 and the lower edge 5 is shaped to accommodate the nose of the player and to rest on the cheeks of the player.

The strap has an adjustment buckle 6 and is connected between side limbs 1a and 1b of the screen 1.

From FIG. 2 it can be seen that the ribs 3a and 3b have the effect of moving the impact point of a squash ball with the screen 1 forwardly of the eyes so that, even allowing for the distortion of a fast moving squash ball on impact with the screen, no part of the ball can contact an eye of the player.

Additional vertical ribs (shown dotted) can be provided to further strengthen the screen immediately in front of each eye, and the slit 3 may be divided into two parts, one for each eye, by a connecting piece which joins the ribs 3a and 3b midway between the ends of the slit 3. Such a connecting piece, in addition to protecting the nose of the wearer, reduces the possibility of the edge of a racquet entering the slits far enough to damage an eye. Typical dimensions for the slit 3 would be a length of 150 mm and a width of 20 mm. The maximum depth of the screen from forehead to cheek would generally be around 60 mm. The dimensions x and y (see FIG. 2) would be around 10 mm and 7 mm, respectively, and the thickness of the unstrengthened regions of the screen 3 would be 2 mm, thinning over the cheeks for comfort of the wearer.

The second embodiment of protector, the rigid part of which is shown in FIGS. 3 to 7, differs from the first in a number of respects, but does share features in common with the first embodiment and these common features have been designated with the same numerals used in FIG. 1 but with the addition of a prime.

The screen 1' in FIG. 3 is moulded in one piece from polycarbonate to have the head-embracing curved shape shown, the side limbs 1a' and 1b' being connected, in use, by a flexible attachment strap (not shown) secured to the screen by way of the openings 7. A slit is provided in the screen 1' in front of each eye, only the right-hand slit 3r' being shown in FIGS. 4, 5 and 6. Each eye slit is flanked above and below by thickened regions in the form of ribs 3a', 3b', respectively, formed integrally with, but standing proud of the front surface of the screen 1'. The upper rib 3a' has a maximum height (6 mm) along a region (marked A) directly in front of the wearer's eye and tapers down (along a region marked B') to a minimum height (2.5 mm) and (along a region marked B) to an intermediate height (3 mm). The lower rib 3b' tapers (over region B") from the intermediate to the minimum height and then remains at the minimum height (2.5 mm) throughout. The two ribs have a uniform thickness t (3 mm). In its unstrengthened regions the screen 1' has a thickness of 3 mm. If the maximum distance between the ribs 3a' and 3b' as measured transversely across either eye slit (i.e. the dimension shown by z in FIG. 4) is 26 mm, with the rib configurations shown, the eyes of the wearer are protected from contact by even the fastest moving squash ball likely to be experienced in a game of squash. The maximum length of each slit is around 90 mm.

The lower edge 5' of the screen 1' is shaped to lie comfortably on the nose of the wearer.

The protectors shown in the drawings are just two embodiments within the scope of the invention and the designs illustrated can be varied in a number of respects. Thus, for example, the shape of the ribs can be changed and the lower rib can be removed altogether. The illustrated arrangements of a smaller rib below rather than above the slit is advantageous since the possibility of ball intrusion into the slit is reduced if the ribs are of different heights in the critical eye region.

What is claimed is:

1. A squash player's eye protector comprising a slitted screen of transparent plastics material and means to support the screen across the face of a squash player to overlie the eye region of a player's face, said screen being formed with a first rigid thickened region on the outwardly facing surface of the screen defining the upper extremity of the salt and a second rigid thickened region on the outwardly facing surface of the screen defining the lower extremity of the slit, said first and second thickened regions being spaced apart at widest part of said slit by a distance which is at least 20 mm but which is less than the diameter of a squash ball, and the first thickened region defining the upper extremity of the slit projects forwardly further than the second thickened region.

2. A squash player's eye protector comprising a curved screen of transparent plastics material and an elasticated strap for supporting the screen on the head of a squash player so that the screen overlies the eye region of the face of the player, means defining an opening in the screen in front of each eye of the player, a first rib defining the upper extremity of each opening and projects forwardly of the screen away from the face of the player, a second rib defining the lower extremity of each opening, said second rib also projects forwardly of the screen away from the face of the player but by a lesser amount than said first rib, the spacing apart of the ribs at the widest part of each opening being at least 20 mm and each rib being such that a squash ball is prevented from contacting an eye of the player through either opening, irrespective of the angle of approach of the ball to the screen or the speed of that approach.

3. An eye protector as claimed in claim 2, wherein the maximum distance between said first rib and said second rib is 26 mm.

4. An eye protector as claimed in claim 2, wherein said first rib has a maximum height of 6 mm and said second rib has a height between 2.5 mm and 3 mm.

* * * * *